United States Patent [19]

Ali

[11] Patent Number: 4,724,229
[45] Date of Patent: Feb. 9, 1988

[54] ARG-ARG-ARG-VASOPRESSIN ANTAGONISTS

[75] Inventor: Fadia E. Ali, Cherry Hill, N.J.

[73] Assignee: Smithkline Beckman Corporation, Philadelphia, Pa.

[21] Appl. No.: 913,439

[22] Filed: Sep. 30, 1986

[51] Int. Cl.$^4$ .......................... C07K 7/16; A61K 37/34
[52] U.S. Cl. ..................................... 514/11; 514/807; 530/315
[58] Field of Search ..................... 517/11, 87; 530/315

[56] References Cited

U.S. PATENT DOCUMENTS

| | | | |
|---|---|---|---|
| 4,469,679 | 9/1984 | Huffman et al. | 514/11 |
| 4,481,193 | 11/1984 | Ali et al. | 514/11 |
| 4,481,194 | 11/1984 | Ali et al. | 514/11 |
| 4,649,130 | 3/1987 | Manning et al. | 514/11 |

OTHER PUBLICATIONS

Chem. Abstracts 88337y, Moore et al.
Chem Abstracts 117716, Moore et al.
M. Manning et al. Peptides, Struce and Function Proc. 9th Ann Peptide Sym. Deber. C. M. et al. eds. Pierce Chemical Co. Rockford Illinois 1985 pp. 599–602.
M. Manning et al., *Nature*, 308, 652 (1984).

*Primary Examiner*—Delbert R. Phillips
*Attorney, Agent, or Firm*—Janice E. Williams; Stuart R. Suter; Alan D. Lourie

[57] ABSTRACT

Vasopressin antagonists which have a tripeptide side chain comprised of three basic amino acids, such as arginine, lysine or ornithine, demonstrate potent $V_1$ and $V_2$-antagonist activity. A species of the invention, which is prepared by conventional peptide sequencing, is [1-($\beta$-mercapto-$\beta$,$\beta$-cyclopentamethylenepropionic acid)-2-(O-ethyl)-D-tyrosine-4-valine-7-arginine-8-arginine-9-arginine]-vasopression.

30 Claims, No Drawings

ARG-ARG-ARG-VASOPRESSIN ANTAGONISTS

FIELD OF THE INVENTION

This invention relates to cyclic nonapeptide compounds which exhibit potent vasopressin antagonist activity. This invention further relates to a pharmaceutical composition and method for producing vasopressin antagonist activity in patients in need thereof.

BACKGROUND OF THE INVENTION

The compounds of this invention exhibit $V_1$ and/or $V_2$ vasopressin antagonist activity. Vasopressin is known to contribute to the antidiuretic mechanism of actions within the kidney. The action of these compounds antagonizes that of the natural anti-diuretic hormone (ADH) so as to cause the body to excrete water.

M. Manning et al., Nature, 308 652 (1984) and U.S. Pat. No. 4,469,679 have disclosed that the terminal glycine unit at the 9-position of certain vasopressin-like antagonists can be removed or replaced by L or D-Ala, Ser or Arg without necessarily affecting the binding at vasopressin receptors.

U.S. Pat. Nos. 4,481,194 and 4,481,193 have disclosed that removing proline at position 7 or both proline and glycine at positions 7 and 9 from the structures of vasopressin antagonist compounds will produce compounds which retain substantial, but somewhat reduced, antagonist activity.

The compounds of this invention have structures which are distinguished over the prior art in that three basic amino acid units, such as arginine, lysine or ornithine are attached directly to the disulfide vasopressin-like ring. The compounds of this invention are potent vasopressin antagonists.

SUMMARY OF THE INVENTION

According to this invention, there are provided cyclic nonapeptides which exhibit potent vasopressin antagonist activity. The structures of these nonapeptides are distinguished by having a tripeptide tail which is composed of three basic amino acid units, such as arginine, lysine or ornithine, and which is directly attached to the cysteine unit of a vasopressin-like ring.

DESCRIPTION OF THE INVENTION

The basic vasopressin antagonist compounds of this invention are illustrated by the following structural formula:

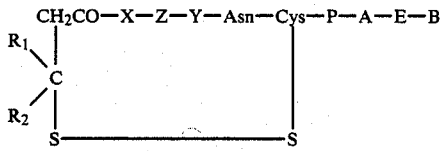

in which:

P is a D or L isomer of Arg, Lys, Orn, HArg, MeArg, MeLys or MeHArg;

A is a D or L isomer of Arg, Lys, Orn, HArg, MeArg, MeLys or MeHArg;

E is a D or L isomer of Arg, Lys, Orn, HArg, MeArg, MeLys or MeHArg;

B is OH, NH$_2$ or NHAlk;

Z is Phe, 4'-Alk Phe, O-Alk Tyr, Ile or Tyr;

X is a D or L isomer of Phe, 4'-Alk Phe, Val, Nva, Leu, Ile, Pba, Nle, Cha, Abu, Met, Chg, Tyr or O-Alk Tyr;

Y is Val, Ile, Abu, Ala, Chg, Gln, Lys, Cha, Nle, Thr, Phe, Leu or Gly; and $R_1$ and $R_2$ are, each, hydrogen, methyl, ethyl or, when taken together, a cycloalkylene ring of 4 to 6 members taken with the $\beta$-carbon to which they are attached.

A subgeneric group of compounds of this invention contains compounds of formula I in which P is Arg, A is Arg, E is Arg and B is NH$_2$. In formula I, $R_1$ and $R_2$ are, preferably, cyclopentamethylene.

Also included in this invention are additional salts, complexes or prodrugs such as esters of the compounds of this invention when B is OH, especially the nontoxic, pharmaceutically acceptable acid addition salts. The acid addition salts are prepared in standard manner in a suitable solvent from the parent compound and an excess of an acid, such as hydrochloric, hydrobromic, sulfuric, phosphoric, acetic, maleic, succinic, ethanedisulfonic or methanesulfonic acids. The end products of formula I have three strong basic groups in their structures, therefore, their acid addition salt derivatives are easily prepared. The ester derivatives of the acid form of the end products, such as the methyl, ethyl or benzyl esters, are prepared as known in the art.

In the description herein and in the claims, the nomenclature common in the art of peptide and vasopressin chemistry is used. When no configuration is noted, the amino acid unit is in the L, or naturally occurring, form. In certain structural formulas, the thio members of the Cap, Mpa and Cys units are added for clarity.

The peptide art designations contained herein are as follows: Cap, $\beta$-mercapto-$\beta$,$\beta$-cycloalkylenepropionic acid; Pmp, $\beta$-mercapto-$\beta$,$\beta$-cyclopentamethylenepropionic acid; Mpr, $\beta$-mercapto-propionic acid; dPen, $\beta$-mercapto-$\beta$,$\beta$-dimethylpropionic acid or desaminopenicillamine; O-Alk Tyr, O-alkyltyrosine; Abu, $\alpha$-amino-n-butyric acid; Chg, cyclohexylglycine; Cha, cyclohexylalanine; Pba, $\alpha$-aminophenylbutyric acid; Gln, glutamic acid amide or glutamine; Gly, glycine; Tyr, tyrosine; Phe, phenylalanine; 4'-Alk Phe, 4'-alkylphenyl-alanine; MeAla, N-methylalanine; Val, valine; Ile, isoleucine; Nle, norleucine; Leu, leucine; Ala, alanine; Lys, lysine; Arg, arginine; HArg, homoarginine; MeArg, N-methyl arginine; MeHArg, N-methylhomoarginine; MeLys, N-methyllysine; Met, methionine; Orn, ornithine; Asn, asparagine; Sar, sarcosine; Tos, tosylate; ClZ,2-chlorobenzyloxycarbonyl; BHA, benzhydrylamine; DMAP, 4-dimethylaminopyridine; DIEA, diisopropylethylamine; HF, hydrogen fluoride; 4-MeBzl, 4-methylbenzyl; TFA, trifluoroacetic acid; DCC, dicyclohexylcarbodiimide; Boc, t-butyloxycarbonyl; Z, benzyloxycarbonyl; VSP, vasopressin; HBT, hydroxybenzotriazole; ACM, acetamidomethyl; Mpa, noncyclic $\beta$-mercaptopropionic acids. In the definitions such as MeArg above, Me denotes a methyl located on the amido nitrogen of the peptide unit concerned.

"Alk" represents a lower alkyl of 1 to 4 carbons. For example, these may be optionally attached to the oxygen substituent of a tyrosine unit at position 2, to the N-terminal nitrogen of the tail, or to the 4'-positon of a Phe unit at position 3. Such alkyl substituents include methyl, ethyl, n-propyl, isopropyl or butyl. The preferred alkyl substituent is ethyl.

The end products (I) of this invention are prepared by oxidation of the following linear nonapeptide:

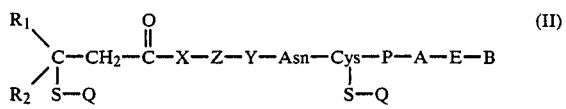

(II)

in which X, Z, Y, P, A, E, B, $R_1$ and $R_2$ are as defined for formula I above. The mercapto groups are members of the units at positions 1 and 6. Each Q is a hydrogen or a displaceable protective group such as acetamidomethyl (ACM). The dithiol of formula II may also be oxidized in the form of an ester or amide derivative at position 9. For example, the amide may be those peptides of Formula II in which B is —NHAlk or —NH$_2$. The esters may include B in which B is O-Alk or O-Benzyl.

The oxidation is carried out using an excess of an alkali metal ferricyanide, such as potassium or sodium ferricyanide, with the linear intermediate II. A suitable unreactive solvent, perferably an aqueous-miscible solvent at a neutral pH, of about 7 to about 7.5, is used. Reaction is carried out at ambient temperature or lower until the reaction is substantially complete. Preferably, the concentrations of the linear peptide dimercaptan and the oxidizing agent are low, such as about 0.01 to about 0.1 molar concentration of oxidizing agent in several liters of aqueous solution to cyclize about 1 to about 5 grams of dimercaptan.

Other mild oxidation agents having an oxidation potential roughly equivalent to ferricyanide may also be used for the ring closure reaction. Oxygen passage through the reaction solution for several days, iodine in methanol, hydrogen peroxide or oxidation in the presence of cupric salts are such alternatives. Cyclization, also, occurs when a displaceable, thiol-protective group such as that at the mercaptan group of the Pmp unit is displaced intramolecularly.

An especially useful thio protective group is acetamidomethyl (ACM). Iodine/alcohol is used for direct, one-pot cyclization of the bis-ACM-S linear peptide.

Of course, one skilled in the art would recognize that certain cyclization methods are not appropriate if an interfering reaction site is present in the structure of the starting material of formula II. The linear mercaptan starting material may have common protective groups temporarily present at the various linear units.

The peptide chain of the linear peptides is usually built up, stepwise, proceeding from the E unit and working toward the Mpa or Pmp unit. Each unit is properly protected as known in the peptide art and as described below. The sequence of step-reactions is conveniently carried out in a Beckman 990B peptide synthesizer or its equivalent without isolation of each intermediate peptide. The details of the procedure are in the working examples presented hereinafter.

The various amino acids (AA), which are consecutively added to the resin-supported chain, are protected as known in the art. For example, the Boc protecting group is used for an amino group, especially at the α-position; an optionally substituted benzyl, for the mercapto groups at the Pmp, Mpa or Cys units; tosyl for the Arg, HArg or MeArg unit; and an optionally substituted benzyloxycarbonyl (Z) for the Tyr or Lys units. The protective groups are, most conveniently, those which are not easily removed by using mild acid treatment, such as for removing the Boc group. Rather, it is preferable to use HF, sodium-liquid ammonia or, for benzyl or benzyloxycarbonyl groups, catalytic hydrogenation.

The resin supported peptide may be treated with an excess of anhydrous hydrogen fluoride with an appropriate scavenger compound, such as anisole, to produce the linear peptide intermediate of formula II in good yield.

The compounds of formula I are also prepared by reacting the Arg acid with a protected form of A and E (as the acid or amide) in any standard peptide method of synthesis. The starting material 7-arginine acids, such as those of formula I in which P is an arginine-like unit as defined above and A is hydroxy; are prepared as described above by a resin-supported or solution reaction sequence.

The compounds of Formula 1 have $V_1$ and/or $V_2$ vasopressin antagonist activity. Vasopressin is known to contribute to the anti-diuretic mechanism of action within the kidney. When the action of these compounds antagonizes that of the natural anti-diuretic hormone (ADH), the body excretes water due to an increased permeability of the terminal portions of the renal tubule. The mechanism of action is at the vasopressin receptors ($V_2$-receptors) located on the plasma membrane of certain renal epithelial cells. The most notable pharmacodynamic effect of the ADH antagonists of this invention is that of a water diuretic, or aquaretic, rather than of a natriuretic such as hydrochlorothiazide.

$V_2$-antagonistic activity toward the natural anti-diuretic hormone (anti-ADH activity) is determined, in vitro, in the medullary tissue of hog or human kidneys and, in vivo, in the hydropenic rat. The in vitro assay procedures for vasopressin stimulated adenylate cyclase activation or vasopressin binding activity are described by F. Stassen et al., J. Pharmacology and Experimental Therapeutics, 223, 50–54 (1982). $V_1$-antagonistic activity is determined by procedures using the rat thoracic aorta tissue and plasma membranes of rat liver. These procedures are described in the noted Stassen publication and in a publication at the 1st International Conference on Diuretics, Miami, Fla., March (1984). Oxytocin antagonism is determined as described by W. Sawyer et al., Endocrinology, 106 81 (1979).

A patient suffering from the syndrome of inappropriate antidiurectic hormone secretion (SIADH) or from an undesirable edematous condition is a target for the compounds of this invention. Examples of clinical conditions for which the compounds of this invention may be used include hypertension, hepatic cirrhosis, hyponatremia, congestive heart failure or a component of any traumatic condition resulting from serious injury or disease. The compounds of formula I in which $R_1$ and $R_2$ form a 5 or 6 membered ring are especially potent $V_2$-antagonists.

The second group of vasopressin receptor sites are the vascular pressor sites ($V_1$-receptors) within the cardiovascular system itself. These may also be antagonized by the compounds of this invention. The congeners of formula I in which $R_1$ and $R_2$ are hydrogen or methyl are potent $V_1$-antagonists. These compounds also have substantial anti-oxytocic activity.

The compounds of this invention, therefore, are used especially to induce anti-hypertensive, anti-oxytocic or diuretic activity in patients in need of such treatment. The compounds are administered internally, parenterally, buccally or by insufflation, in a nontoxic but effective quantity, preferably dispersed in a pharmaceutical carrier. Dosage units of the active ingredient are selected from the range of about 0.01 to about 10 mg/kg, prefereably about 0.1 to about 1 mg/kg, of base based on a 70 kg patient. The dosage units are administered to the human or animal patient from about 1 to about 5 times daily.

Pharmaceutical compositions which contain an active antagonist ingredient of forumla I, comprise a dosage unit which is dissolved or suspended in a standard liquid carrier, such as isotonic saline, and is contained in an ampoule or multiple dose vial suitable for a parenteral injection such as for intravenous, subcutaneous or intramuscular administration. A composition for insufflation may be similar but is usually administered in a metered dose applicator or inhaler. Pulverized powder compositions may, also, be used along with oily preparations, gels, buffers for isotonic preparations, buccal losenges, trans-dermal patches and emulsions or aerosols.

Hydropenic Rat Screen

The assay for anti-ADH activity in vivo is the hydropenic rat protocol described in the examples below.

For a period of approximately 18 hours prior to testing, food and water is not administered to the male rats which will be used in the testing. The rats are placed in a cage in a ratio of 4 per metabolism cage.

At 0 hours, the test compound is administered intraperitoneally to the test group while an equivalent volume of vehicle is administered to both control groups (fasted and non-fasted). Urine volume and osmolality of the test and control groups are measured every hour for 4 hours. Test values are recorded as ml of urine excreted (cumulative), mEg/rat electrolyte excreted, mg/rat urea excreted, and osmolality in milliOsmoles/Kg $H_2O$. A tolerance test is used to determine significance. ED 300 is defined as the dose of compound ($\mu$g/Kg) required to lower urine osmolality to 300 m-Osmoles/Kg.

Table 1 below exhibits the potent vasopressin antagonist activity of the nonapeptide of the present invention having a tripeptide tail which is composed of three basic amino acid units, arginine.

TABLE I

Biological Activity of Vasopressin Analogs

| No. | X | $K_{bind}$ (nM)[a] | $K_i$ (nM)[b] | $ED_{300}$ ($\mu$g/ml)[c] | $K_{bind}$ human liver membranes $V_1$ (nM)[d] |
|---|---|---|---|---|---|
| 1 | Arg—Arg—Arg—$NH_2$ | 2.6 | 1.54 | 22.1 ± 4.6 | 4.41 |
| 2 | Arg—$NH_2$ | 9.1 | 2.5 | 58 | 1.3 |
| 3 | Arg—Arg—$NH_2$ | 3.4 | 1.7 | 7.2 | 1.3 |
| 4 | Pro—Arg—$NH_2$ | 11 | 4.5 | 9.8 | 1.08 |

[a]$K_{bind}$ is a measure of the affinity of a ligand for a receptor in the porcine renal medullary membrane. It is derived from the equation for competitive inhibition $K_b$ = $IC_{50}/(1 + L/K_D)$ where $IC_{50}$ is the concentration of the ligand for 50% inhibition of [$^3$H]—LVP binding, L is the concentration of the ligand, and $K_D$ is the dissociation constant of [$^3$H]—LVP.
[b]$K_i$ is the inhibition constant measured for inhibition of LVP stimulated adenylate cyclase of pig kidney medullary membrane, and is derived from the equation for competitive inhibition as described.
[c]$Ed_{300}$ is the dose ($\mu$g/kg) required to decrease urine osmolality in rats from the hydropenic levels (1500 mOsm/kg $H_2O$) to 300 mOsm/kg $H_2O$.
[d]$K_{bind}$ is a measure of the affinity of a ligand for a receptor in the human liver membrane tissue. It is derived from the equation in [a] above.

EXAMPLES

Examples provided are intended to assist in a further understanding of the invention. Particular materials employed, species and condition, are intended to be further illustrative of the invention and not limitative of the reasonable scope thereof.

EXAMPLE 1

The vasopressin antagonist compound [1-($\beta$-mercapto-$\beta$,$\beta$-cyclopentamethylenepropionic acid)-2-(O-ethyl)-D-tyrosine-4-valine-7-arginine-8-arginine-9-arginine]-vasopressin was represented by the following structural formula:

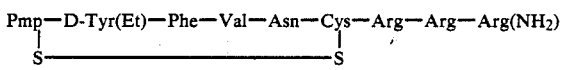

The protected peptide-resin intermediate, Pmp-(4-MeBzl)-D-Tyr(Et)-Phe-Val-Asn-Cys(4-MeBzl)-Arg(Tos)-Arg(Tos)-Arg(Tos)-BHA was synthesized by solid-phase methods on the automated synthesizer Beckman 990 B using 1.0 g of benzhydrylamine resin (approx. 0.62 mmol). All amino acids were protected as tert.-butyloxycarbonyl (Boc) on the nitrogen and were activated by DCC/HBT for sequential coupling. The Pmp(4-MeBzl) was coupled using DMAP. The peptide was cleaved from the resin with simultaneous deprotection of the side-chain protecting groups using anhydrous HF (30 ml) in the presence of anisole (3.0 mL) at 0° C. for 60 minutes. After evaporation in vacuo to dryness, the residue containing peptide was washed with anhydrous ether. The crude peptide was extracted with dimethylformamide (DMF) (100 mL) and 40% acetic acid (HOAc) (100 mL) into 3.5 liters of degassed water which had been adjusted to a pH of 4.5. The aqueous diluted disulfhydryl nonapeptide mixture was oxidatively cyclized with 110 mL of potassium ferricyanide ($K_3Fe(CN)_6$), (0.01 M) at a pH of 7.2. The pH of the solution was adjusted to 4.5 using glacial acetic acid (HOAc). The solution was passed through a weakly acid acrylic resin (Bio-Rex 70) column. The column was eluted with pyridine-acetate buffer (30:4:66, pyridine/glacial acetic acid/water/ v/v). The pyridine acetate was removed by distillation in vacuo. The residue was lyophilized from dilute acetic acid to give 913.5 mg of partially purified crude peptide.

Purification (1) Partition Column, Sephadex G-25

Sample: 191 mg, n-Butanol/Acetic Acid/water (n-BuOH/HOAc/$H_2O$), 4:1:5;
 (a) 108.40 mg;
 (b) 33.72 mg.

(2) Gel-filtration

Sephadex G-15, 0.2 M HOAc, used 80 mg, from (1-A) to obtain;
 (2a) 51 mg;
 (2b) 12.08 mg.

Physical Data

M.F.: $C_{58}H_{91}N_{19}O_{11}S_2$
M.wt: 1293.64
FAB: $(M+H)^+$ 1294

AAA: Asp (1.00), Cys (0.66); Val (1.03), Tyr (0.86), Phe (1.31), Arg (3.2)

Peptide Content 69.8%

Chromatography Data

1. Thin layer chromatography (TLC)

(a) n-Butanol/Acetic Acid/Water/Ethyl Acetate (B/A/W/E) (1:1:1:1: v/v) $R_f$ 0.53

(b) n-Butanol/Pyridine/Acetic Acid/water (B/P/A/W) (15:10:3:3 v/v) $R_f$ 0.48

2. High pressure liquid chromatography (HPLC), Altex Ultrasphere ODS, 5μ, 0.45 mm×25 cm (a) Gradient 80:20 to 50:50 of 0.1% aqueous TFA/CH₃CN

K'=12

(b) Isocratic 55:45 of 0.1% aqueous TFA/CH₃CN

K'=5.17

The following examples are intended to demonstrate the preparation and use of the compounds of this invention.

EXAMPLE 2

Substituting a stoichiometric quantity of Boc-L-Tyr(Et) for Boc-D-Tyr(Et) at the 2 unit of the peptide synthesis of Example 1 gives cyclized

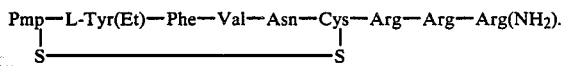

Substituting in Example 1, Boc-D-Ile for Boc-D-Tyr(Et) at the 2 unit gives

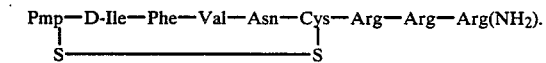

Substituting Boc-L-Phe(4-Me) for the amino acid at the 3 unit and Boc-Nle at the 4 unit in the synthesizer sequence reactions of Example 1 gives

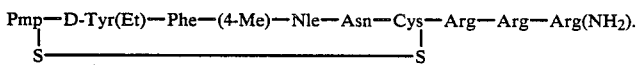

Substituting Boc-Cha at the 4 unit gives

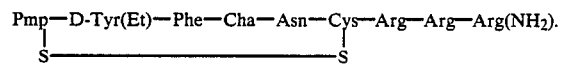

Substituting unprotected Gln at position 4 using HBT gives

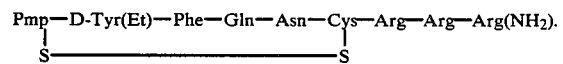

Substituting Boc-D-Pba at the 2 unit and Boc-Chg at the 4 unit of the detailed reaction sequence of Example 1 gives

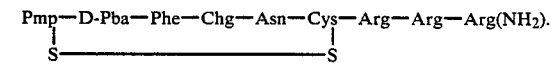

EXAMPLE 3

Substituting the appropriate protected ring units in the synthetic sequence of formula I gives the respective nonapeptide or a salt thereof as follows:

a. [1-desaminopenicillamine-2-(O-ethyl)-D-tyrosine-3-(4'-methylphenlalanine)-7-arginine-8-arginie-9-arginine]-vasopressin acetate;

b. [1-(β-mercaptopropionic acid)-2-(O-ethyl)-D-tyrosine-4-(α-aminobutyric acid)-7-arginine-8-arginine-9-arginine]-vasopressin;

c. [1-(β-mercaptopropionic acid)-2-valine-4-cyclohexylglycine-7-arginine-8-arginine-9-arginine]-vasopressin hydrochloride;

d. [1-(β-mercaptopropionic acid)-4-glutamine-7-arginine-8-homoarginine-9-arginine]-vasopressin;

e. [1-desaminopenicillamine-2-phenylalanine-7-homoarginine-8-homoarginine-9-arginine]-vasopressin;

f. [1-desaminopenicillamine-2-D-α-amiophenylbutyric acid-4-isoleucine-7-arginine-8-arginine-9-arginine]-vasopressin;

g. [1-desaminopenicillamine-2-tryptophan-4-glutamine-7-D-arginine-8-D-arginine-9-arginine]-vasopres h. [1-(β-mercapto-β,β-cyclopentamethylenepropionic acid)-2-tyrosine-3-(4'-methylphenylalanine)-7-arginine-8-arginine-9-arginine]-vasopressin;

i. [1-(β-mercaptopropionic acid)-2-(O-ethyl)-D-tyrosine-3-isoleucine-4-threonine-7-arginine-8-arginine-9-arginine]-vasopressin acetate.

EXAMPLE 4

The vasopressin antagonist compound [1-(β-mercapto-β,β-cyclopentamethylenepropionic acid)-2-(O-ethyl)-D-tyrosine-4-valine-7-ornithine-8-ornithine-9-ornithine]-vasopressin is represented by the following structural formula:

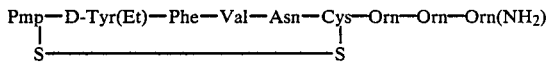

The protected peptide-resin intermediate, Pmp-(4-MeBzl)-D-Tyr(Et)-Phe-Val-Asn-Cys(4-MeBzl)-Orn(ClZ)-Orn(ClZ)-Orn(ClZ)-BHA is synthesized by solid-phase methods on the automated synthesizer Beckman 990 B using 1.0 g of benzhydrylamine resin (approx. 0.62 mmol). All amino acids are protected as tert.-butyloxycarbonyl (Boc) on the nitrogen and are activated by DCC/HBT for sequential coupling. The Pmp(4-MeBzl) is coupled using DMAP. The peptide is cleaved from the resin with simultaneous deprotection of the side-chain protecting groups using anhydrous HF (30 ml) in the presence of anisole (3.0 mL) at 0° C. for 60 minutes. After evaporation in vacuo to dryness, the residue containing peptide is washed with anhydrous ether. The crude peptide is extracted with dimethylformamide (DMF) (100 mL) and 40% acetic acid (HOAc) (100 mL) into 3.5 liters of degassed water which has been adjusted to a pH of 4.5. The aqueous diluted disulfhydryl nonapeptide mixture is oxidatively cyclized with 110 mL of potassium ferricyanide (K₃Fe(CN)₆), (0.01 M) at a pH of 7.2. The pH of the solution is adjusted to 4.5 using glacial acetic acid (HOAc). The solution is passed through a weakly acid acrylic resin (Bio-Rex 70) column. The column is eluted with pyridine-acetate buffer (30:4:66, pyridine/glacial acetic acid/water/ v/v). The pyridine acetate was removed by distillation in vacuo. The residue is lyophilized from dilute acetic acid to give the product of partially purified crude peptide.

EXAMPLE 5

The vasopressin antagonist compound [1-(β-mercapto-β,β-cyclopentamethylenepropionic acid)-2(O-ethyl)-D-tyrosine-4-valine-7-lysine-8-lysine-9lysine-]-vasopressin is represented by the following structural formula:

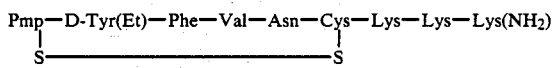

The protected peptide-resin intermediate, Pmp-(4-MeBzl)-D-Tyr(Et)-Phe-Val-Asn-Cys(4-MeBzl)-Lys(ClZ)-Lys(ClZ)-Lys(ClZ)-BHA is synthesized by solid-phase methods on the automated synthesizer Beckman 990 B using 1.0 g of benzhydrylamine resin (approx. 0.62 mmol). All amino acids are protected as tert.-butyloxycarbonyl (Boc) on the nitrogen and are activated by DCC/HBT for sequential coupling. The Pmp(4-MeBzl) is coupled using DMAP. The peptide is cleaved from the resin with simultaneous deprotection of the side-chain protecting groups using anhydrous HF (30ml) in the presence of anisole (3.0 mL) at 0° C. for 60 minutes. After evaporation in vacuo to dryness, the residue containing peptide is washed with anhydrous ether. The crude peptide is extracted with dimethylformamide (DMF) (100 mL) and 40% acetic acid (HOAc) (100 mL) into 3.5 liters of degassed water which has been adjusted to a pH of 4.5. The aqueous diluted disulfhydryl nonapeptide mixture is oxidatively cyclized with 110 mL of potassium ferricyanide ($K_3Fe(CN)_6$), (0.01 M) at a pH of 7.2. The pH of the solution is adjusted to 4.5 using glacial acetic acid (HOAc). The solution is passed through a weakly acid acrylic resin (Bio-Rex 70) column. The column is eluted with pyridine-acetate buffer (30:4:66, pyridine/glacial acetic acid/water/ v/v). The pyridine acetate is removed by distillation in vacuo. The residue is lyophilzed from dilute acetic acid to give the product of partially purified crude peptide.

EXAMPLE 6

The vasopressin antagonist compound [1-(β-mercapto-β,β-cyclopentamethylene propionic acid)-2(O-ethyl)-D-tyrosine-4-valine-7-arginine-8-lysine-9-ornithine]-vasopressin is represented by the following structural formula:

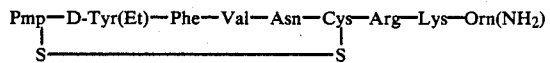

The protected peptide-resin intermediate, Pmp-(4-MeBzl)-D-Tyr(Et)-Phe-Val-Asn-Cys(4-MeBzl)-Arg(Tos)-Lys(ClZ)-Orn(ClZ)-BHA is synthesized by solid-phase methods on the automated synthesizer Beckman 990 B using 1.0 g of benzhydrylamine resin (approx. 0.62 mmol). All amino acids are protected as tert.-butyloxycarbonyl (Boc) on the nitrogen and are activated by DCC/HBT for sequential coupling. The Pmp(4-MeBzl) is coupled using DMAP. The peptide is cleaved from the resin with simultaneous deprotection of the side-chain protecting groups using anhydrous HF (30 ml) in the presence of anisole (3.0 mL) at 0° C. for 60 minutes. After evaporation in vacuo to dryness, the residue containing peptide is washed with anhydrous ether. The crude peptide is extracted with dimethylformamide (DMF) (100 mL) and 40% acetic acid (HOAc) (100 mL) into 3.5 liters of degassed water which has been adjusted to a pH of 4.5. The aqueous diluted disulfhydryl nonapeptide mixture is oxidatively cyclized with 110 mL of potassium ferricyanide ($K_3Fe(CN)_6$), (0.01 M) at a pH of 7.2. The pH of the solution is adjusted to 4.5 using glacial acetic acid (HOAc). The solution is passed through a weakly acid acrylic resin (Bio-Rex 70) column. The column is eluted with pyridine-acetate buffer (30:4:66, pyridine/glacial acetic acid/water/ v/v). The pyridine acetate is removed by distillation in vacuo. The residue is lyophilized from dilute acetic acid to give the product of partially purified crude peptide.

EXAMPLE 7

Parenteral Dosage Unit Compositions

A preparation which contains 0.10 mg of the peptide of Example 1 as a sterile dry powder for parenteral injection is prepared as follows: 0.5 mg of peptide is dissolved in 1 ml of an aqueous solution of 20 mg of mannitol. The solution is filtered under sterile conditions into a 2 ml ampoule and lyophilized. The reconstituted solution is administered to a patient in need of vasopressin antagonist treatment as necessary, from 1-5 times daily by injection, or in an equivalent continuous i.v. drip injection.

Nasal Dosage Unit Compositions 2.5 Mg of a finely ground peptide of this invention, such as the product of Example 2, is suspended in a mixture of 75 mg of benzyl alcohol and 1.395 g of a suspending agent such as a commercial mixture of semi-synthetic glycerides of higher fatty acids. The suspension is placed in an aerosol 10 ml container which is closed with a metering valve and charged with aerosol propellants. The contents comprise 100 unit doses which are administered intranasally to a subject in need thereof from 1-6 times a day.

I claim:

1. A compound having the formula:

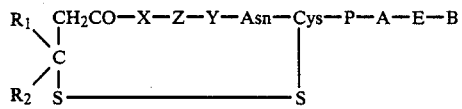

in which:

P is a D or L isomer of Arg, Lys, Orn, HArg, MeArg, MeLys or MeHArg;

A is a D or L isomer of Arg, Lys, Orn, HArg, MeArg, MeLys or MeHArg;

E is a D or L isomer of Arg, Lys, Orn, HArg, MeArg, MeLys or MeHArg;

B is OH, $NH_2$ or NHAlk;

Z is Phe, 4'-Alk Phe, O-Alk Tyr, Ile or Tyr;

X is a D or L isomer of Phe, 4'-Alk Phe, Val, Nva, Leu, Ile, Pba, Nle, Cha, Abu, Met, Chg, Tyr or O-Alk Tyr;

Y is Val, Ile, Abu, Ala, Chg, Gln, Lys, Cha, Nle, Thr, Phe, Leu or Gly; and $R_1$ and $R_2$ are, each, hydrogen, methyl, ethyl or, when taken together and with the $\beta$-carbon to which they are attached, a cycloalkylene ring of 4 to 6 members; and wherein Alk is an alkyl of 1 to 4 carbons;

or a pharmaceutically acceptable salt or prodrug thereof.

2. The compound according to claim 1 in which $R_1$ and $R_2$, taken together, form a spiropentamethylene ring.

3. The compound according to claim 1 in which P-A-E-B is Arg-Arg-Arg(NH$_2$).

4. The compound according to claim 1 in which P-A-E-B is Orn-Orn-Orn(NH$_2$).

5. The compound according to claim 1 in which P-A-E-B is Lys-Lys-Lys(NH$_2$).

6. The compound according to claim 1 in which P-A-E-B is Arg-Lys-Orn(NH$_2$).

7. The compound of claim 1 in which the compound is 1-($\beta$-mercapto-$\beta,\beta$-cyclopentamethylenepropionic acid)-2-(O-ethyl)-D-tyrosine-4-valine-7-arginine-8-arginine-9arginine]-vasopressin or a pharmaceutically acceptable, acid addition salt thereof.

8. The compound of claim 1 in which the compound is 1-($\beta$-mercapto-$\beta,\beta$-cyclopentamethylenepropionic acid)-2-(O-ethyl)-D-tyrosine-4-valine-7-D-arginine-8-D-arginine-9-D-arginine]-vasopressin or a pharmaceutically acceptable, acid addition salt thereof.

9. The compound of claim 1 in which the compound is [1-($\beta$-mercapto-$\beta,\beta$-cyclopentamethylenepropionic acid)-2-(O-methyl)-L-tyrosine-4-valine-7-arginine-8-D-arginine-9-D-arginine]-vasopressin or a pharmaceutically acceptable, acid addition salt thereof.

10. The compound of claim 1 in which the compound is [1-($\beta$-mercaptopropionic acid)-2-(O-ethyl)-D-tyrosine-3-isoleucine-4-threonine-7-arginine-8-arginine-9-arginine]-vasopressin or a pharmaceutically acceptable, acid addition salt thereof.

11. The compound of claim 1 in which the compound is 1-($\beta$-mercapto-$\beta,\beta$-cyclopentamethylenepropionic acid)-2-(O-ethyl)-D-tyrosine-4-valine-7-D-arginine-8-arginine-9-arginine]-vasopressin or a pharmaceutically acceptable, acid addition salt thereof.

12. The compound of claim 1 in which the compound is [1-($\beta$-mercaptopropionic acid)-2-(O-ethyl)-D-tyrosine-4-valine-7-N-methylarginine-8-arginine-9-arginine]-vasopressin or a pharmaceutically acceptable, acid addition salt thereof.

13. The compound of claim 1 in which the compound is [1-($\beta$-mercapto-$\beta,\beta$-cyclopentamethylenepropionic acid)-2-(O-ethyl)-D-tyrosine-4-valine-7-N-methyl-arginine-8-D-arginine-9-arginine]-vasopressin or a pharmaceutically acceptable, acid addition salt thereof.

14. The compound of claim 1 in which the compound is [1-($\beta$-mercapto-$\beta,\beta$-cyclopentamethylenepropionic acid)2-(O-ethyl)-D-tyrosine-4-valine-7-arginine-8-arginine-9-N-methylarginine]-vasopressin or a pharmaceutically acceptable, acid addition salt thereof.

15. The compound of claim 1 in which the compound is [1-($\beta$-mercapto-$\beta,\beta$-cyclopentamethylenepropionic acid)-2-(O-ethyl)-D-tyrosine-4-valine-7-arginine-8-lysine-9-arginine]-vasopressin or a pharmaceutically acceptable, acid addition salt thereof.

16. The compound of claim 4 in which the compound is [1-($\beta$-mercapto-$\beta,\beta$-cyclopentamethylenepropionic acid)-2-(O-ethyl)-D-tyrosine-4-valine-7-ornithine-8-ornithine-9-ornithine]-vasopressin or a pharmaceutically acceptable, acid addition salt thereof.

17. The compound of claim 5 in which the compound is [1-($\beta$-mercapto-$\beta,\beta$-cyclopentamethylenepropionic acid)-2-(O-ethyl)-D-tyrosine-4-valine-7-lysine-8-lysine-9-lysine]-vasopressin or a pharmaceutically acceptable, acid addition salt thereof.

18. The compound of claim 6 in which the compound is [1-($\beta$-mercapto-$\beta,\beta$-cyclopentamethylenepropionic acid)-2-(O-ethyl)-D-tyrosine-4-valine-7-arginine-8-lysine-9-ornithine]-vasopressin or a pharmaceutically acceptable, acid addition salt thereof.

19. A pharmaceutical composition having vasopressin antagonist activity comprising a pharmaceutical carrier and, dispersed therein, an effective therefor but nontoxic quantity of the compound of claim 1.

20. A pharmaceutical composition having vasopressin antagonist activity comprising a pharmaceutical carrier and, dispersed therein, an effective therefor but nontoxic quantity of the compound of claim 3.

21. A pharmaceutical composition having vasopressin antagonist activity comprising a pharmaceutical carrier and, dispersed therein, an effective therefor but nontoxic quantity of the compound of claim 7.

22. A method of producing vasopressin antagonist activity in a patient in need thereof which comprises administering parenterally or intranasally to the patient an effective therefor, nontoxic quantity of the compound of claim 1.

23. A method of producing vasopressin antagonist activity in a patient in need thereof which comprises administering parenterally or intranasally to the patient an effective therefor, nontoxic quantity of the compound of claim 3.

24. A method of producing vasopressin antagonist activity in a patient in need thereof which comprises administering parenterally or intranasally to the patient an effective therefor, nontoxic quantity of the compound of claim 7.

25. A method of treating congestive heart failure in a patient in need thereof which comprises administering parenterally or intranasally to the patient an effective therefor, nontoxic quantity of the compound of claim 1.

26. A method of treating congestive heart failure in a patient in need thereof which comprises administering parenterally or intranasally to the patient an effective therefor, nontoxic quantity of the compound of claim 3.

27. A method of treating congestive heart failure in a patient in need thereof which comprises administering parenterally or intranasally to the patient an effective therefor, nontoxic quantity of the compound of claim 7.

28. A method of treating hypertension in a patient in need thereof which comprises administering parenterally or intranasally to the patient an effective therefor, nontoxic quantity of the compound of claim 1.

29. A method of treating hypertension in a patient in need thereof which comprises administering parenterally or intranasally to the patient an effective therefor, nontoxic quantity of the compound of claim 3.

30. A method of treating hypertension in a patient in need thereof which comprises administering parenterally or intranasally to the patient an effective therefor, nontoxic quantity of the compound of claim 7.

* * * * *